United States Patent
Moore et al.

(10) Patent No.: US 8,674,139 B2
(45) Date of Patent: Mar. 18, 2014

(54) PROCESS FOR MAKING TERTIARY AMINOALCOHOL COMPOUNDS

(75) Inventors: David W. Moore, Hebron, IL (US); Raymond J. Swedo, Mount Prospect, IL (US); Asghar A. Peera, Cary, IL (US)

(73) Assignee: ANGUS Chemical Company

( * ) Notice: Subject to any disclaimer, the term of this patent is extended or adjusted under 35 U.S.C. 154(b) by 0 days.

(21) Appl. No.: 13/819,098

(22) PCT Filed: Sep. 21, 2011

(86) PCT No.: PCT/US2011/052566
§ 371 (c)(1),
(2), (4) Date: Feb. 26, 2013

(87) PCT Pub. No.: WO2012/044508
PCT Pub. Date: Apr. 5, 2012

(65) Prior Publication Data
US 2013/0172622 A1    Jul. 4, 2013

Related U.S. Application Data

(60) Provisional application No. 61/386,664, filed on Sep. 27, 2010.

(51) Int. Cl.
*C07C 209/00*    (2006.01)

(52) U.S. Cl.
USPC .......................................... 564/495; 564/448

(58) Field of Classification Search
None
See application file for complete search history.

(56) References Cited

U.S. PATENT DOCUMENTS 3,651,144 A * 3/1972 Tindall et al. ................. 564/495

OTHER PUBLICATIONS

Bobowski et al (Journal of Heterocyclic Chemistry, 1979), 16(8), 1525-34).*
Wheatley, Alpha, alpha-Dimethylcholine: Esters and Carbamates, Journal of the American Chemical Society, vol. 76, May 1954, pp. 2832-2835.
Sreedhar et al., Direct One-Pot Reductive Amination of Aldehydes with Nitroarenes in a Domino Fashion: Catalysis by Gum-Acacia-Stabalized Palladium Nanoparticles, Journal of Organic Chemistry, vol. 74, Aug. 2009, pp. 8806-8809.

* cited by examiner

*Primary Examiner* — Sudhakar Katakam

(57) ABSTRACT

Provided is a process for making a tertiary aminoalcohol compound. The process comprises using an excess amount of a carbonyl compound in a condensation step between the carbonyl compound and a nitroalkane, and conducting a hydrogenation/alkylation step to produce the tertiary aminoalcohol. The process uses fewer steps than conventional processes.

10 Claims, No Drawings

PROCESS FOR MAKING TERTIARY AMINOALCOHOL COMPOUNDS

CROSS REFERENCE TO RELATED APPLICATIONS

This is a §371 application of PCT International Patent Application No. PCT/US2011/052566 filed Sep. 21, 2011, and claims priority from Provisional Application Ser. No. 61/386,664, filed Sep. 27, 2010, each of which is incorporated herein by reference in its entirety.

FIELD OF THE INVENTION

The invention relates to an improved process for making tertiary aminoalcohol compounds.

BACKGROUND OF THE INVENTION

Tertiary aminoalcohol compounds play an important role in a variety of commercial and consumer products. For instance, they may be used as neutralizers in paints and coatings, in process water applications, and personal care and cosmetics formulations, as emulsifying agents, as corrosion inhibitors, e.g., in metalworking fluids, as resin solubilizers, foam catalysts, finish stabilizers, and/or as raw materials for chemical synthesis of other useful materials.

Tertiary aminoalcohol compounds are generally prepared on a commercial scale from nitroalkanes by a four step process. The condensation reaction (Henry Reaction) between aldehyde and nitroalkane forms the nitroalcohol. Catalytic reduction (hydrogenation) produces the corresponding aminoalcohol. A purification step (crystallization or distillation) eliminates impurity carryover to the final product. Finally a reductive alkylation (2nd hydrogenation) step produces the tertiary aminoalcohol.

It would be an advance in the art if new processes were developed that provided advantages over the known processes, such as reducing the number of process steps, increasing yield, and/or reducing manufacturing costs.

BRIEF SUMMARY OF THE INVENTION

The invention provides a process for making a tertiary aminoalcohol compound of formula I:

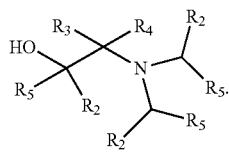

The process comprises:
(a) reacting a nitroalkane compound of formula IV

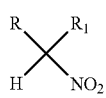

with a molar excess of a carbonyl compound of formula III

in the presence of a basic catalyst to form an intermediate product mixture comprising free carbonyl compound of formula III and a nitroalcohol compound of formula II

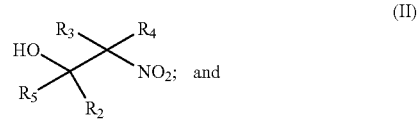

(b) hydrogenating the intermediate product mixture in the presence of hydrogen and a hydrogenation catalyst such that the nitroalcohol compound of formula II and the free compound of formula III react therein to form the tertiary aminoalcohol compound of formula I.

DETAILED DESCRIPTION OF THE INVENTION

As noted above, the invention provides a process for making a tertiary aminoalcohol compound. The process exhibits various advantages over conventional processes. In particular, according to some embodiments, the invention may be conducted without the necessity of isolation and/or purification of the intermediate compounds, thus resulting in fewer process steps. In addition, the process of the invention may result in formation of the desired product in higher yield than conventional systems. Further, the process may also result in additional cost savings, aside from the fixed cost savings from eliminating two process steps and the savings from increased yield, because as described below only one fresh charge of hydrogenation catalyst is needed instead of two charges as in the conventional process.

According to the process, a nitroalkane compound is reacted with a molar excess of a carbonyl compound to form an intermediate product mixture. The intermediate product mixture contains a nitroalcohol compound and free unreacted carbonyl compound. The mixture is hydrogenated/alkylated in the presence of hydrogen and a hydrogenation catalyst such that the hydrogen, the nitroalcohol compound and the free carbonyl compound in the mixture react to form the desired tertiary aminoalcohol compound.

The starting nitroalkane of the process is a compound of the formula IV:

wherein R and $R_1$ are independently H, $C_1$-$C_6$ alkyl, or $C_3$-$C_{12}$ cycloalkyl. In some embodiments, R and $R_1$ are both H. In some embodiments, R is H and $R_1$ is $C_1$-$C_6$ alkyl, alternatively $C_1$-$C_3$ alkyl, alternatively ethyl, or alternatively methyl. In some embodiments, R and $R_1$ are both independently $C_1$-$C_6$ alkyl. In some embodiments, both are n-propyl, alternatively ethyl, or alternatively methyl. In some embodiments, R and $R_1$ together with the carbon to which they are attached form $C_3$-$C_{12}$ cycloalkyl, alternatively $C_4$-$C_7$ cycloalkyl, or alternatively cyclohexyl. In some embodiments, the nitroalkane compound is nitromethane, nitroethane, 1-nitropropane, 2-nitropropane, or nitrocyclohexane.

The starting carbonyl compound of the process is a material of the formula III:

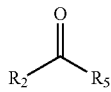
(III)

wherein $R_2$ is H or $C_1$-$C_6$ alkyl; and $R_5$ is H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl. In some embodiments, $R_2$ and $R_5$ are both H. In some embodiments, $R_2$ is H and $R_5$ is $C_1$-$C_6$ alkyl, alternatively $C_1$-$C_3$ alkyl, alternatively ethyl, or alternatively methyl. In some embodiments, $R_2$ and $R_5$ are both independently $C_1$-$C_6$ alkyl, alternatively they are independently $C_1$-$C_3$ alkyl. In some embodiments, $R_2$ is H and $R_5$ is $C_3$-$C_{12}$ cycloalkyl, alternatively $C_4$-$C_7$ cycloalkyl, or alternatively cyclohexyl. In some embodiments, $R_2$ and $R_5$ together with the carbon to which they are attached form $C_3$-$C_{12}$ cycloalkyl, alternatively $C_4$-$C_7$ cycloalkyl, or alternatively cyclohexyl. In some embodiments, the compound is formaldehyde.

In the invention process, the carbonyl compound of formula III and the nitroalkane of formula IV undergo a base catalyzed condensation reaction in which the carbonyl compound reacts with the hydrogen atoms attached to the nitro-bound carbon of the nitroalkane, replacing each such hydrogen with an alkanol substituent. The reaction product is a nitroalcohol compound, contained in the intermediate product mixture.

The conditions for the condensation reaction may be readily determined by a person skilled in the art. As an example of a typical process, the carbonyl compound and a base catalyst may be mixed in a reaction vessel and the mixture heated to elevated temperature (e.g., using applied heating and/or the reaction exotherm if present), such as to about 30 to 90° C., alternatively to about 40 to 85° C. The nitroalkane compound may then be added incrementally over a period of time, such as over about 1 to 8 hours, alternatively over about 2-4 hours, or as a continuous process. Following complete addition, continued stirring and heating or cooling, such as at about 40 (40) to 90 (90)° C. alternatively to at about 60-75° C., may be applied, for instance for 1 to 3 hours, to drive the reaction to the desired level of completion.

Various base catalysts may be used in the condensation reaction and include, for instance, inorganic bases (e.g., sodium hydroxide, calcium hydroxide) or organic tertiary amines. The tertiary amines are preferred, particularly triethylamine. The concentration of the basic catalyst may be in the range of, for example, 0.2 to 2.0 percent by weight, based on the weight of the nitroalkane.

A solvent may optionally be used in the reaction. Suitable solvents are those that do not substantially interfere with the formation of the desired product. Examples include, for instance, lower alcohols such as methanol, ethanol, n-propanol, or isopropanol.

The nitroalcohol formed in the condensation reaction between the nitroalkane and the carbonyl compound may be represented by the following formula II:

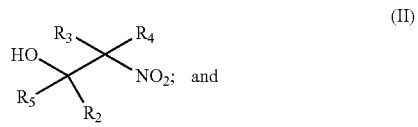

wherein $R_2$ and $R_5$ are as defined above (including the various embodiments thereof), and $R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl.

In some embodiments, $R_3$ and $R_4$ in the formula II compounds are both independently $C_1$-$C_6$ alkyl, or they are independently $C_1$-$C_3$ alkyl. In some embodiments, both are n-propyl, alternatively ethyl, or alternatively methyl. In some embodiments, $R_3$ and $R_4$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula II compounds is —C(OH)$R_2R_5$, and $R_2$ and $R_5$ are both H. In some embodiments, $R_3$ is —C(OH)$R_2R_5$, $R_2$ is H and $R_5$ is $C_1$-$C_6$ alkyl, alternatively $C_1$-$C_3$ alkyl, alternatively ethyl, or alternatively methyl. In some embodiments, $R_3$ is —C(OH)$R_2R_5$, $R_2$ is H and $R_5$ is $C_3$-$C_{12}$ cycloalkyl, alternatively $C_4$-$C_7$ cycloalkyl, or alternatively cyclohexyl. In some embodiments, $R_3$ is —C(OH)$R_2R_5$, and $R_2$ and $R_5$ are both independently $C_1$-$C_6$ alkyl, alternatively they are independently $C_1$-$C_3$ alkyl. In some embodiments, $R_3$ is —C(OH)$R_2R_5$, and $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula II compounds is —C(OH)$R_2R_5$ and $R_4$ is $C_1$-$C_6$ alkyl, alternatively $C_1$-$C_3$ alkyl, alternatively ethyl, or alternatively methyl.

An important aspect of the invention process is that the intermediate product mixture that contains the formula II nitroalcohol also contains free carbonyl compound of formula III. The free carbonyl compound functions, in the hydrogenation/alkylation step of the process, to react with the nitroalcohol to form the desired tertiary aminoalcohol.

In order to provide an intermediate product mixture that contains free carbonyl compound, according to the invention, an amount of the carbonyl compound in excess of that required for completion of the condensation reaction described above is used. As a result, the unreacted formula III carbonyl compound remains present in the intermediate product mixture and is therefore available for the hydrogenation/alkylation step.

In order to achieve reasonable yield and to reduce formation of undesired byproducts, it is preferred that a sufficient amount of formula III carbonyl compound be used in the condensation reaction step such that, following completion of that reaction, the intermediate product mixture contains at least 2 moles of free formula III carbonyl compound per mole of formula II nitroalcohol compound in the intermediate product mixture.

The amount of the carbonyl compound to be used in the condensation step to provide such excess can be readily calculated by those skilled in the art, and will depend primarily on the number of hydrogens in the nitroalkane compound that are available for the condensation reaction. By way example, 2-nitropropane will generally react with one mole of carbonyl compound in the condensation reaction. Therefore, in order to provide an intermediate product mixture that contains at least 2 moles of free carbonyl compound per mole of nitroalcohol, at least 3 moles of the carbonyl compound per mole of nitroalkane may be used in the condensation reaction. Similarly, for nitromethane, at least five equivalents of the carbonyl compound may be used for each equivalent of the nitroalkane. For nitroethane and 1-nitropropane, at least four equivalents of the carbonyl compound may be used.

Formation of the desired tertiary aminoalcohol is achieved by hydrogenating/alkylating the intermediate product mixture in the presence of hydrogen and a hydrogenation catalyst such that the nitroalcohol compound of formula II, the free carbonyl compound of formula III, and the hydrogen react to yield the tertiary aminoalcohol.

The hydrogenation/alkylation reaction is carried out in the presence of hydrogen gas in combination with a hydrogenation catalyst, for example, Raney nickel or a platinum or palladium based catalyst (Pt or Pd in elemental form or as oxides, with or without supports, e.g., carbon). Preferred is Raney nickel.

Hydrogenation/alkylation conditions may be readily determined by those skilled in the art. By way of example, a temperature range of about 30-170° C., alternatively about 100-120° C., and a pressure of about 100-1000 psi (690 kPa-6900 kPa) may be used. The concentration of catalyst may vary, and is typically between about 1 and 25 weight percent, based on the nitroalcohol. A solvent may be used, such as methanol. The hydrogenation reaction is continued until the desired amount of product is formed, preferably to completion, which is typically 1 to 12 hours.

Optionally, the process of the invention may further include a final aldehyde/ketone trim step following the hydrogenation/alkylation. In this optional step, additional carbonyl compound of formula III is slowly fed into the hydrogenation/alkylation product mixture, and the resultant mixture held at temperature for an additional time, e.g., 1-3 hours. The trim step may help further increase the alkylation to desired product, thus potentially increasing overall product yield.

Preferably, following the hydrogenation/alkylation reaction, the intermediate product mixture contains at least 0.5 percent, alternatively at least 5 percent, alternatively at least 10 percent, or alternatively at least 20 percent by weight of the desired tertiary aminoalcohol. The tertiary aminoalcohol may be filtered to separate it from the catalyst. Additional workup may be carried out, such as vacuum removal of excess solvent, and/or distillation of the tertiary aminoalcohol.

The tertiary aminoalcohol prepared according to the invention is a compound of the formula I:

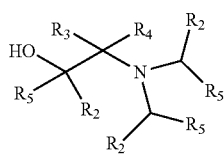

(I)

wherein $R_2$ is H or $C_1$-$C_6$ alkyl; $R_5$ is H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; $R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl.

In some embodiments of the invention, $R_2$ and $R_5$ in the formula I compounds are both H. In some embodiments, $R_2$ is H and $R_5$ is $C_1$-$C_6$ alkyl, alternatively $C_1$-$C_3$ alkyl, alternatively ethyl, or alternatively methyl. In some embodiments, $R_2$ and $R_5$ are both independently $C_1$-$C_6$ alkyl, alternatively they are independently $C_1$-$C_3$ alkyl. In some embodiments, $R_2$ is H and $R_5$ is $C_3$-$C_{12}$ cycloalkyl, alternatively $C_4$-$C_7$ cycloalkyl, or alternatively cyclohexyl. In some embodiments, $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ and $R_4$ in the formula I compounds are both independently $C_1$-$C_6$ alkyl, or they are independently $C_1$-$C_3$ alkyl. In some embodiments, both are n-propyl, alternatively ethyl, or alternatively methyl. In some embodiments, $R_3$ and $R_4$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula I compounds is —C(OH)$R_2R_5$, and $R_2$ and $R_5$ are both H. In some embodiments, $R_3$ is —C(OH)$R_2R_5$, $R_2$ is H and $R_5$ is $C_1$-$C_6$ alkyl, alternatively $C_1$-$C_3$ alkyl, alternatively ethyl, or alternatively methyl. In some embodiments, $R_3$ is —C(OH)$R_2R_5$, $R_2$ is H and $R_5$ is $C_3$-$C_{12}$ cycloalkyl, alternatively $C_4$-$C_7$ cycloalkyl, or alternatively cyclohexyl. In some embodiments, $R_3$ is —C(OH)$R_2R_5$, and $R_2$ and $R_5$ are both independently $C_1$-$C_6$ alkyl, alternatively they are independently $C_1$-$C_3$ alkyl. In some embodiments, $R_3$ is —C(OH)$R_2R_5$, and $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula I compounds is —C(OH)$R_2R_5$ and $R_4$ is $C_1$-$C_6$ alkyl, alternatively $C_1$-$C_3$ alkyl, alternatively ethyl, or alternatively methyl.

Preferred compounds of formula I include: 2-(dimethylamino)-2-methyl-1-propanol, N,N-dimethyltris(hydroxymethyl)aminomethane, 2-(dimethylamino)-2-ethylpropane-1,3-diol, 2-(dimethylamino)-2-methylpropane-1,3-diol or 1-(dimethylamino)cyclohexyl-methanol.

Tertiary aminoalcohols prepared according to the invention may be used in a variety of applications. For instance, they may be used as neutralizers in paints and coatings, process water applications, and personal care and cosmetics formulations, as emulsifying agents, as corrosion inhibitors, e.g., in metalworking fluids, as resin solubilizers, foam catalysts, finish stabilizers, and/or as raw materials for chemical synthesis of other useful materials.

"Alkyl" as used in this specification encompasses straight and branched chain aliphatic groups having the indicated number of carbon atoms. If no number is indicated (e.g., aryl-alkyl-), then 1-6 alkyl carbons are contemplated. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), and $C_2$-$C_6$ alkene. Unless otherwise indicated, the foregoing substituent groups are not themselves further substituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), and $C_2$-$C_6$ alkene. A preferred substituent is $C_1$-$C_6$ alkyl. Unless otherwise indicated, the foregoing substituent groups are not themselves further substituted.

The following examples are illustrative of the invention but are not intended to limit its scope. Unless otherwise indicated, the ratios, percentages, parts, and the like used herein are by weight.

EXAMPLES

Example 1

Preparation of
2-(dimethylamino)-2-methyl-1-propanol (DMAMP)

Conversion of 2-nitropropane (2-NP) to 2-nitro-2-methyl-1-propanol (NMP).

3 equivalents of methyl formcel are charged to a reaction flask. The reaction is catalyzed with 0.65 mole % triethylamine (TEA), which is added to the methyl formcel. The methyl formcel/TEA mixture is heated to 85° C. and the 2-NP is added incrementally over approximately 2 hours. The reaction is followed by a one hour hold period at 85° C. to complete conversion. At 60° C., a 2 hour hold time is needed for complete conversion.

Conversion of NMP to DMAMP. NMP is converted to DMAMP by a stepwise reduction with hydrogen to form 2-amino-2-methyl-1-propanediol (AMP). The AMP is not isolated but reacted in situ with the excess formaldehyde (from step 1) so that DMAMP is continuously being formed throughout the hydrogenation. Upon completion, and depending on the temperature during the NMP feed, the temperature is increased to promote methylation. GC scans of in-process samples show multiple peaks. These various compounds are not impurities but rather intermediates, including the monooxazolidine of AMP, the monomethylated AMP, and the monooxazolidine of MMAMP. After 1 hour at elevated temperature, a methyl formcel trim is slowly fed to the autoclave. After the methyl formcel trim, the reactor is held at temperature for an additional hour to complete the methylation.

For higher yield and product purity, the NMP feed is preferably carried out at the lowest practical temperature (see reaction #1 in the table below). To simplify the process, in reaction #2, all autoclave steps are carried out at 100° C. This reaction also works well although, as would be expected at higher nitroalcohol feed temperatures, there is some yield loss, indicated by the higher level of N,N-dimethylisopropylamine (DMIPA). For further simplification of the process, the NMP may be fed at 65° C. and cooling water shut off at different points to allow the reaction exotherm to increase the temperature prior to the methyl formcel trim (to complete the methylation).

GC-MS CI [M+H]=118 with retention time 8.07 min, confining the formation of DMAMP. GC analysis indicates conversion to DMAMP of between 88% and 97%, depending on the specific reaction conditions used.

Example 2

Preparation of
N,N-dimethyltris(hydroxymethyl)aminomethane (DMTA)

Conversion of nitromethane (NM) to tris(hydroxymethyl)nitromethane (TN). 5 equivalents of methyl formcel are charged to the reaction flask. The reaction is catalyzed with 0.4 mole % triethylamine (TEA), which is added to the methyl formcel. NM (1.0 molar eq.) is fed into this mixture at such a rate so as to keep the temperature between 45-50° C. Once the NM has been added, the reaction mixture is stirred for an additional hour. During this time, no external cooling is applied and the temperature will drop slowly.

Conversion of TN to DMTA. An analogous procedure as described in Example 1 is followed to convert TN to DMTA. GC-MS CI [M+H]=150 with retention time 21.40 min, confirming the formation of DMTA.

Example 3

Preparation of
1-(dimethylamino)cyclohexylmethanol

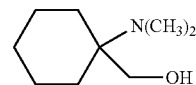 [SMILES: CN(C)C1(CO)CCCCC1]

A 2-liter 3-neck flask equipped with a magnetic stirrer, nitrogen blanket, thermocouple controlled heating mantle and addition funnel is charged with methyl Formcel (55 wt. % formaldehyde in methanol/water: 262.66 g/4.81 moles) and with 2 mL of triethylamine. The addition funnel is charged with nitrocyclohexane (193.76 g/1.5 moles). The nitrocyclohexane is added to the Formcel solution over a period of 1.25 hours, while stirring under a nitrogen blanket. During the addition, the reaction temperature is maintained at ca. 45° C. A mild exotherm is noted at the beginning of the addition. After completing the addition, the reaction mixture is heated to 70° C. GC analysis is run after 3 hours at 70° C. and shows >95% conversion to 1-nitrocyclohexanemethanol.

A 2-liter Parr autoclave is charged with methanol (240 g) and Raney Nickel catalyst (R-3111, 50 g wet weight). The reactor is sealed, purged with nitrogen followed by purging with hydrogen and then brought up to 100° C. under 500 psi (3445 kilopascals) hydrogen pressure. With rapid stirring (650-700 rpm), the nitrocyclohexanemethanol solution from above—diluted with an additional 150 mL of methanol—is added over a period of about 3 hours while maintaining the reactor at 100° C./700-750 psi (4823-5168 kilopascals) hydrogen. When the addition is completed, stirring at 100° C./700-750 psi (4823-5168 kilopascals) hydrogen is continued for about 30 minutes, then a sample removed for GC analysis: conversion to product is about 75%. A solution of 50 mL of Formcel and 50 mL of methanol is then added to the reactor over a period of about 45 minutes, maintaining rapid stirring at 100° C./700-750 psi (4823-5168 kilopascals) hydrogen. After this addition is completed, conditions are maintained for 3 hours, then another GC sample is taken: conversion to product increases to 83%. An additional 25 mL of Formcel are added to the reactor over about 30 minutes, then rapid stirring at 100° C./700-750 psi (4823-5168 kilopascals) hydrogen is maintained for about 3.5 hours. A GC sample taken at this point shows 90% conversion to product. After cooling to room temperature, the reactor is vented, opened and the crude product isolated via vacuum filtration.

The clear, peach-colored filtrate is stripped on a rotary evaporator (50° C./29" vacuum), yielding 212 g of clear reddish oil which solidifies to an off-white crystalline solid on cooling. This product is distilled under vacuum giving a clear, colorless, mobile liquid with a boiling point of 129-130°

C./27 ton. A total of 180.6 g are collected (77% yield). The product solidifies on cooling to a white crystalline solid, mp=38-41° C. A GC analysis indicates 97.3% 1-(dimethylamino)-cyclohexylmethanol, with 1.8% of 1-(methylamino) cyclohexanemethanol, and 0.9% of the oxazolidine of 1-aminocyclohexanemethanol.

Example 4

Preparation of 2-(Dimethylamino)-2-methylpropane-1,3-diol

A 500 mL 3-neck flask equipped with a magnetic stirrer, nitrogen blanket, thermocouple controlled heating mantle and addition funnel is charged with methyl Formcel (55 wt. % formaldehyde in methanol/water: 126 g/2.31 moles, 4.2 equivalent) and with 0.5 g of triethylamine. The addition funnel is charged with nitroethane (75 g/1.0 mole, 1 equivalent). The nitroethane is added to the Formcel solution over a period of 45 minutes, while stirring under a nitrogen blanket. During the addition, the reaction temperature is maintained at ca. 60° C. A mild exotherm is noted at the beginning of the addition. After completing the addition, the reaction is let to stir at room temperature overnight. After this time, the reaction is deemed complete and the material used in the hydrogenation/alkylation reaction as-is.

A 2-liter Parr autoclave is charged with methanol (250 g) and Raney Nickel catalyst (R-3111, 50.8 g wet weight). The reactor is sealed, purged with nitrogen followed by purging with hydrogen and then brought up to 45° C. under 500 psi hydrogen pressure. When the temperature reaches the desired mark, the reactor pressure is increased to approximately 700 psi. With rapid stirring (600-640 rpm), the 2-methyl-2-nitropropane-1,3-diol solution from above—diluted with an additional 100 mL of methanol—is added over a period of about 2.5 hours while maintaining the reactor at 45° C./700-750 psi hydrogen. When the addition is completed, stiffing at 45° C./700-750 psi hydrogen is continued for about 30 minutes, and then a sample removed for GC analysis: conversion to product is about 74%.

In order to get the reaction to go to completion fast, the autoclave temperature is increased to 120° C. When the temperature stabilizes, a solution of 40 mL of Formcel and 40 mL of methanol are then added to the reactor at the rate of approximately 2 mL/min over a period of about 50 minutes, maintaining rapid stirring at 120° C./700-750 psi hydrogen. After this addition is completed, conditions are maintained for 1 hour, and then another GC sample taken: conversion to product increased to 91%. An additional 100 mL of Formcel/methanol solution are added to the reactor over a period of 55 minutes, then rapid stirring at 120° C./700-750 psi hydrogen maintained for about 1 hour. A GC sample taken at this point shows 99% conversion to product.

After cooling to room temperature, the reactor is vented, opened and the crude product isolated via vacuum filtration. The colorless, clear filtrate is stripped on a rotary evaporator (50-55° C./29-30" vacuum) to remove water/methanol. The resulting white wet solid is washed with pentane and the solid separated from pentane by aspirator. The material is air dried for about 30 minutes, followed by vacuum oven drying for an additional 6 hours at 50° C. to remove any residual solvents. This process provides approximately 121 g (73% overall yield) of pure DMAMPD with >99% purity. GC-MS CI [M+H]=134 with retention time 10.75 min confirming the formation of the desired product. $^1$H NMR (CDCl$_3$): ∂ 0.93 (s, 3H), 2.32 (s, 6H), 3.57 (s, 4H). $^{13}$C NMR (CDCl$_3$): ∂ 23.74, 49.10, 71.72 and 75.22 ppm. Karl Fisher Titration—0.28% water content. pKa: 9.7.

Example 5

Preparation of 2-(Dimethylamino)-2-ethylpropane-1,3-diol

Using nitroethane and greater than 2 equivalents of formaldehyde (methyl formcel) as starting materials, and following the general procedure of Examples 1 and 2 while making non-critical variations, the title compound may be obtained.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:
1. A process for making a tertiary aminoalcohol compound of formula I:

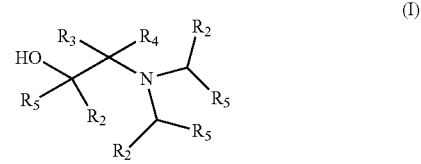

wherein $R_2$ is H or $C_1$-$C_6$ alkyl;
$R_5$ is H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl;
$R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl, the process comprising:
(a) reacting a nitroalkane compound of formula IV

wherein R and $R_1$ are independently H, $C_1$-$C_6$ alkyl, or $C_3$-$C_{12}$ cycloalkyl, or R and $R_1$ together with the carbon to which they are attached form $C_3$-$C_{12}$ cycloalkyl, with a molar excess of a carbonyl compound of formula III

in the presence of a basic catalyst to form an intermediate product mixture comprising free carbonyl compound of formula III and a nitroalcohol compound of formula II

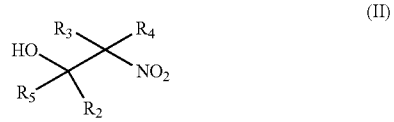

(b) hydrogenating the intermediate product mixture in the presence of hydrogen and a hydrogenation catalyst such that the nitroalcohol compound of formula II and the free carbonyl compound of formula III react therein to form the tertiary aminoalcohol compound of formula I.

2. The process of claim 1 wherein the intermediate product mixture of step (a) comprises at least two moles of free carbonyl compound of formula III per mole of nitroalcohol compound of formula II.

3. The process of claim 1 wherein additional carbonyl compound of formula III is added following step (b).

4. The process of claim 1 wherein $R_3$ and $R_4$ are each independently $C_1$-$C_3$ alkyl.

5. The process of claim 1 wherein $R_3$ and $R_4$ are each —C(OH)$R_2R_5$.

6. The process of claim 1 wherein $R_3$ is —C(OH)$R_2R_5$ and $R_4$ is $C_1$-$C_6$ alkyl.

7. The process of claim 1 wherein $R_3$ and $R_4$ together with the carbon to which they are attached form $C_3$-$C_{12}$ cycloalkyl.

8. The process of claim 1 wherein $R_2$ and $R_5$ are H.

9. The process of claim 1 wherein following step (b), the concentration of the tertiary aminoalcohol compound of formula I in the intermediate product mixture is at least 0.5 percent by weight.

10. The process of claim 1 wherein the compound of formula I is 2-(dimethylamino)-2-methyl-1-propanol, N,N dimethyltris(hydroxymethyl)aminomethane, 2-(dimethylamino)-2-ethylpropane-1,3-diol, 2-(dimethylamino)-2-methylpropane-1,3-diol or 1-(dimethylamino) cyclohexylmethanol.

* * * * *